(12) United States Patent
Murashita

(10) Patent No.: US 7,223,240 B2
(45) Date of Patent: May 29, 2007

(54) ULTRASONIC DIAGNOSTIC APPARATUS

(75) Inventor: Masaru Murashita, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 0 days.

(21) Appl. No.: 10/691,070

(22) Filed: Oct. 22, 2003

(65) Prior Publication Data

US 2004/0097808 A1 May 20, 2004

(30) Foreign Application Priority Data

Nov. 14, 2002 (JP) ............................. 2002-330856

(51) Int. Cl.
*A61B 8/00* (2006.01)
(52) U.S. Cl. .................................... 600/443
(58) Field of Classification Search ........ 600/443–447, 600/453–456; 128/916
See application file for complete search history.

(56) References Cited

U.S. PATENT DOCUMENTS

| | | | | |
|---|---|---|---|---|
| 5,215,093 | A | * | 6/1993 | Miyazaki et al. ............ 600/455 |
| 5,322,067 | A | * | 6/1994 | Prater et al. ................. 600/443 |
| 5,469,850 | A | * | 11/1995 | Iizuka et al. ................ 600/443 |
| 5,528,703 | A | * | 6/1996 | Lee ............................. 382/257 |
| 5,588,435 | A | * | 12/1996 | Weng et al. ................ 600/443 |
| 5,669,385 | A | * | 9/1997 | Pesque et al. .............. 600/453 |
| 5,779,641 | A | * | 7/1998 | Hatfield et al. ............. 600/443 |
| 5,931,784 | A | * | 8/1999 | Kajiwara et al. ........... 600/441 |
| 6,352,509 | B1 | | 3/2002 | Kawagishi et al. |
| 6,436,049 | B1 | * | 8/2002 | Kamiyama et al. ......... 600/458 |
| 2002/0072670 | A1 | | 6/2002 | Chenal et al. |
| 2002/0133075 | A1 | | 9/2002 | Abdehak |

FOREIGN PATENT DOCUMENTS

| | | |
|---|---|---|
| EP | 0 830 842 | 3/1998 |
| EP | 1 008 864 | 6/2000 |
| EP | 1 152 364 | 11/2001 |
| JP | 4-348745 | 12/1992 |

(Continued)

OTHER PUBLICATIONS

T. Yagi, et al., "The effects of a trackball-derived region of interest using acoustic quantification method", *JSUM Proceedings*, Nov. 1993, pp. 517-518.

(Continued)

*Primary Examiner*—Francis J. Jaworski
(74) *Attorney, Agent, or Firm*—Koda & Androlia

(57) ABSTRACT

In an ultrasonic diagnostic apparatus capable of forming a three-dimensional ultrasonic image, an entire cavity portion of an organ can be displayed without any part being invisible. Three-dimensional ultrasonic image data obtained based on an ultrasonic wave transmitted and received with respect to an object organ is stored in a memory 20. With regard to the stored data, a brightness value of each voxel is binarized in a binarization processing section 24 using a predetermined threshold value. Then, the binarized brightness value is further inverted in a brightness value inverting section 26. Consequently, the cavity portion of the organ which has low brightness before inversion has high brightness, and the wall portion of the organ which has high brightness before inversion and which obstruct observation of the inner cavity portion has now low brightness. Thus, solid representation of the cavity portion to be observed can be obtained, thereby facilitating observation.

5 Claims, 5 Drawing Sheets

FOREIGN PATENT DOCUMENTS

| | | |
|---|---|---|
| JP | 9-131345 | 5/1997 |
| JP | 11-56840 | 3/1999 |
| JP | 11-221220 | 8/1999 |
| JP | 2000-300555 | 10/2000 |
| JP | 2002-224116 | 8/2002 |
| JP | 2002-306480 | 10/2002 |

OTHER PUBLICATIONS

T. Taxt, et al., "Noise reduction and segmentation in time-varying ultrasound images", *Proceedings of the International Conference on Pattern Recognition*, Atlantic City, Jun. 15-21, 1990. Conference A: Computer Vision and Conference B: Pattern Recognition Systems and Applications, Los Alamitos, *IEEE Comp. Soc. PRess*, US, Jun. 16, 1990: 591-596.

http://web.archive.org/web/20010914030153/http://www.clevelandclinic.org/cancer/general/glossary/l.htm.

"Automatic Left Ventricular Endocardium Detection in Echocardiograms Based on Ternary Thresholding Method" written by Wataru Ohyama, et al. (pp. 320-323), and published in Sep. 2002 in the U.S. by IEEE Comput. Soc.

\* cited by examiner

ULTRASONIC DIAGNOSTIC APPARATUS

BACKGROUND OF THE INVENTION

1. Field of the Invention

The present invention relates to an ultrasonic diagnostic apparatus for providing an image of a cavity portion of an organ as a three-dimensional image.

2. Description of Related Art

Ultrasonic diagnostic apparatuses which transmit and receive ultrasound with respect to a living body and which then provide a three-dimensional image of inside the living body based on a received ultrasonic signal have been known. In general, the three-dimensional image thus obtained is a solid representation of information concerning a brightness value of each voxel. In this case, however, a cavity portion inside an organ cannot be observed. When observing a heart, for example, a cardiac muscle portion is brightly displayed because ultrasound is reflected by the cardiac muscle of the heart, and no information can be obtained regarding a cavity portion inside the organ, such as the characteristics or behavior of a ventricle. Therefore, in order to observe a cavity portion, a processing is conventionally performed in which a cutting plane is specified and an image of the cavity portion is displayed while information concerning regions in front of the plane is eliminated, for example.

Further, in diagnosis regarding the heart, there is a demand for obtaining a stroke volume of the heart. Conventionally, an approximate stroke volume has been obtained based on a tomogram of the heart or the like. For example, the length of a predetermined portion of the left ventricle is measured and the stroke volume is obtained based on sequential change of this length over time, or, in another example, the cross sectional area of the left ventricle at a certain cutting section is obtained and the stroke volume is calculated based on sequential change in this cross sectional area with time.

When a cavity portion inside an organ is observed, necessary information is often provided by the state of the inner wall surface of the cavity. Accordingly, when a cavity is observed in such a manner that a cutting plane is specified and information concerning regions in front of the cutting plane is eliminated, as conventionally performed, it is not possible to observe the regions of the cavity which have been eliminated.

Further, according to the conventional method, a volume of a cavity portion being observed is only an assumed value based on the length of a predetermined part and the area of a predetermined section. Therefore, an accurate volume cannot be obtained.

SUMMARY OF THE INVENTION

The present invention advantageously provides an ultrasonic diagnostic apparatus capable of preferable observation and information acquisition concerning a cavity portion inside an organ.

An ultrasonic diagnostic apparatus according to an embodiment of the present invention inverts and binarizes the brightness value of each voxel regarding three-dimensional data obtained based on a received ultrasonic signal so as to display a cavity portion of an organ, and provides a three-dimensional image of the cavity portion of the organ. Because the brightness value is inverted, it is possible to observe cavity portions where ultrasound reflection is weak. Further, binarization processing enables reliable extraction of the outline surface of the cavity portion being observed.

It is further possible to provide means for specifying a region of interest for extracting a cavity portion of an organ to be observed with regard to the inverted and binarized data.

Also, it is possible to calculate and provide the volume of the cavity portion of the organ based on a three-dimensional image thereof. Further, it is possible to provide data for supporting diagnosis, such as a change of the volume with time and a ratio between the minimum and maximum values of the volume.

An object organ may be a heart and an object cavity portion may be a left ventricle. Information concerning the cardiac output can be obtained by calculating the volume of the left ventricle.

BRIEF DESCRIPTION OF THE DRAWINGS

These and other objects of the invention will be explained in the description below, in connection with the accompanying drawings, in which.

DETAILED DESCRIPTION OF THE PREFERRED EMBODIMENT

A preferred embodiment of the present invention will be described in further detail with reference to the accompanying drawings. Although a heart, particularly a left ventricle, is described as the object of observation in the following example, the present invention is clearly also applicable to other cardiac cavities and to cavity portions of other organs.

Figure 1:
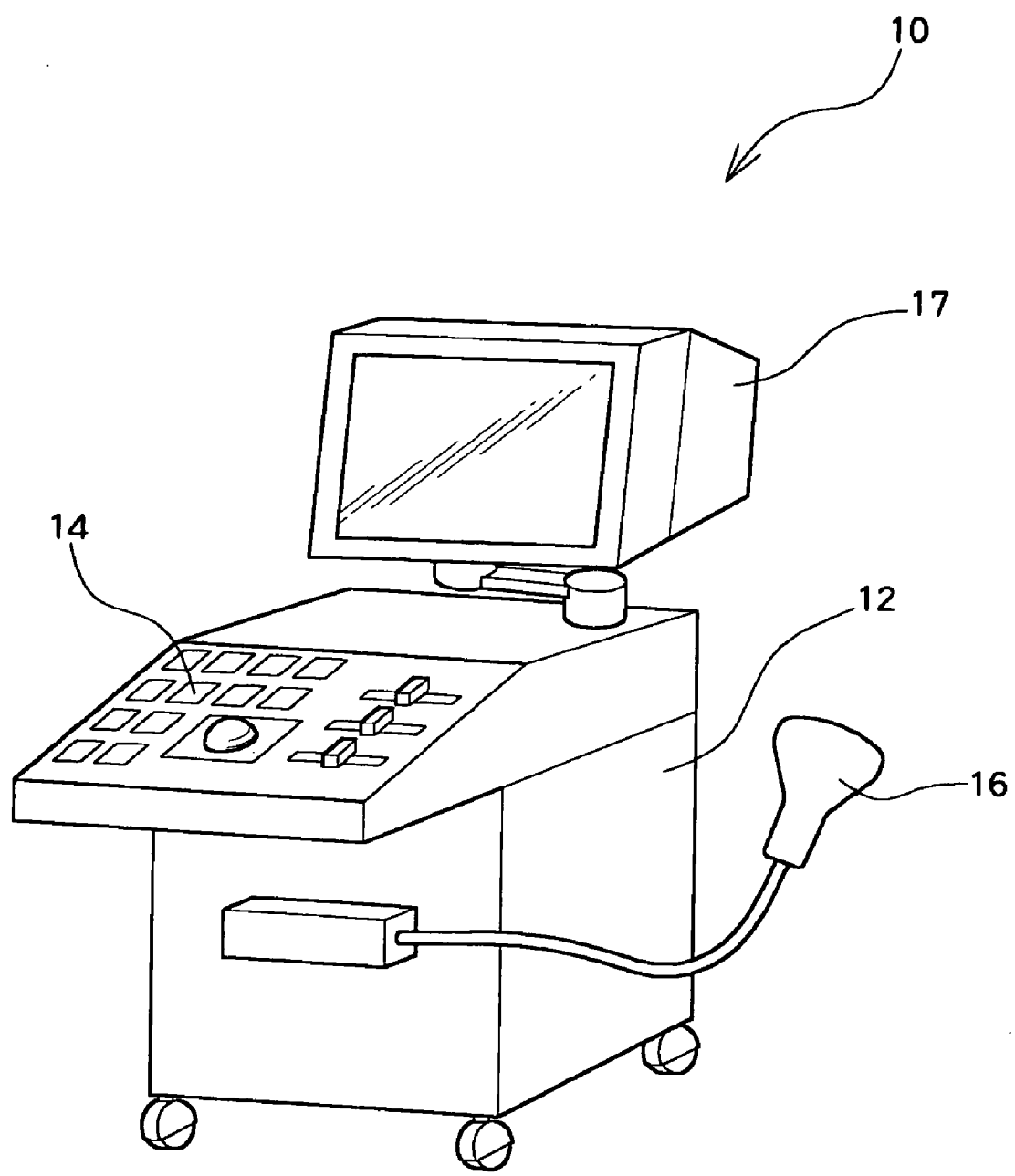
FIG. 1 is a schematic view showing an appearance of an ultrasonic diagnostic apparatus according to an embodiment of the present invention.

FIG. 1 schematically shows an appearance of an ultrasonic diagnostic apparatus 10 according to an embodiment of the present invention. The ultrasonic diagnostic apparatus 10 has a function of forming a three-dimensional ultrasonic image. The ultrasonic diagnostic apparatus 10 includes an operation panel 14 for performing various operations at a front surface of a main body 12 of the apparatus 10. Further, an ultrasonic probe 16 for transmitting and receiving ultrasound with regard to an object is connected via a cable to the apparatus main body 12. A monitor 17 is provided above the apparatus main body 12 for displaying an ultrasonic image or the like obtained based on a reflection wave received by the ultrasonic probe 16. A circuit board in which a circuit for performing transmission/reception of ultrasonic wave, signal processing of received reflection wave, image processing, or the like is incorporated, is provided within the apparatus main body 12.

Figure 2:
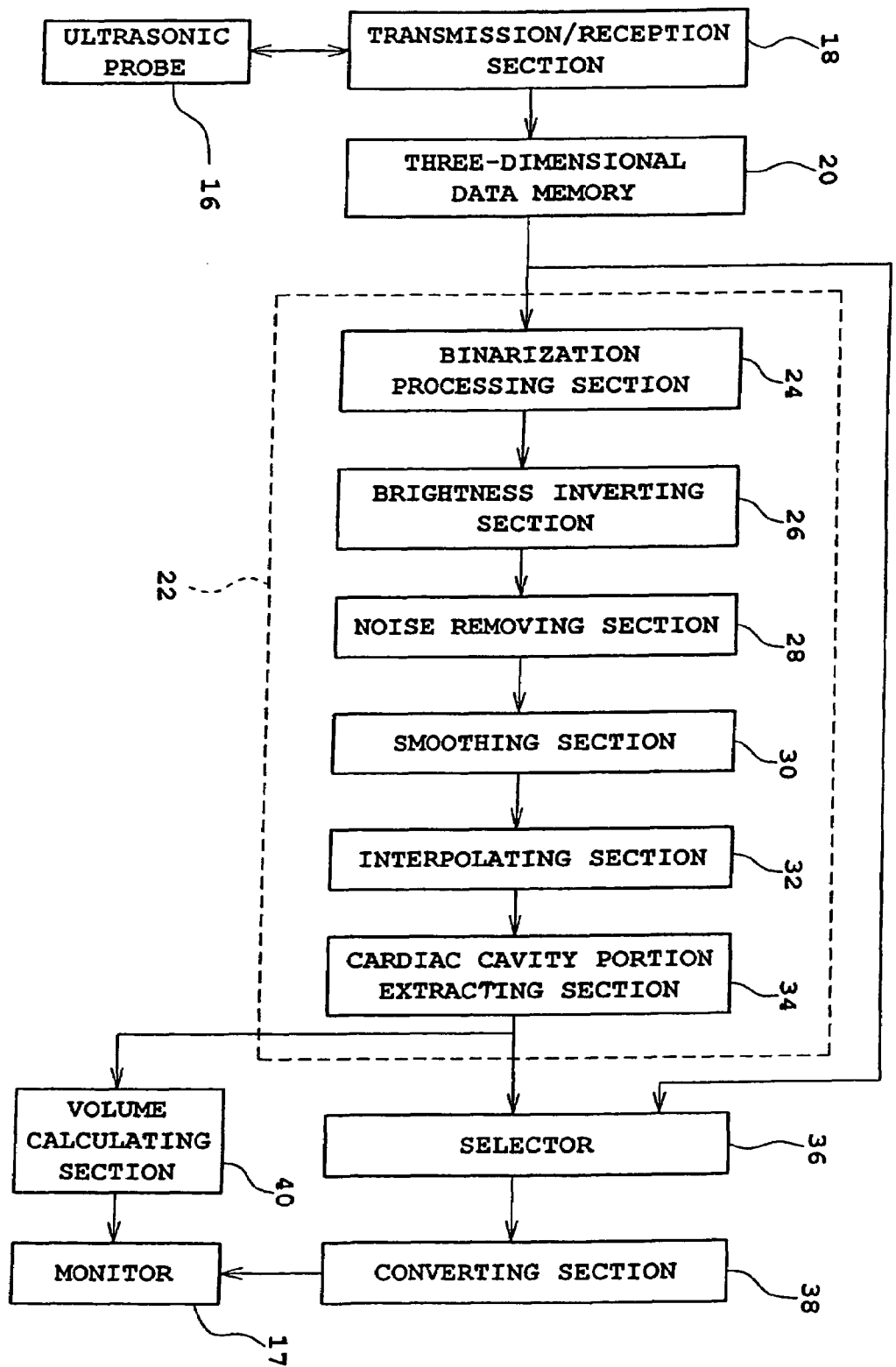
FIG. 2 is a block diagram showing a configuration according to the embodiment of the present invention.

FIG. 2 is a block diagram showing a configuration concerning formation of an ultrasonic image, and specifically shows a configuration related to image processing suitable for displaying a cavity portion of an organ, such, for example, as a cardiac cavity portion including a left ventricle. The ultrasonic probe 16 is capable of scanning in two directions using an ultrasonic beam, which enables formation of a three-dimensional ultrasonic image. A transmission/reception section 18, which corresponds to the ultrasonic probe 16 for three-dimensional image, controls transmission and reception of ultrasonic wave and transmits the received data to a three-dimensional data memory 20 where the data is stored. In an example according to the present embodiment in which the ultrasonic probe 16 is a convex type probe, the three-dimensional data is stored in the form of a polar coordinate system (θ, φ, r) based on a main scanning direction θ of the ultrasonic beam, a sub scanning direction φ orthogonal to the main scanning direction, and a distance r from the center of curvature of a contact surface of the ultrasonic probe 16. The three-dimensional data may also be stored in another form, such as a form obtained by converting the polar coordinate system, which can be obtained directly from reflection wave information, into another coordinate system, such as, for example, a rectangular coordinate system (x, y, z).

The data stored in the three-dimensional data memory 20 has a brightness corresponding to the intensity of reflection wave. When a heart is an observation object, the cardiac muscle portion which causes significant reflection has a high brightness, while the cardiac cavity portion which is filled with fluid (blood) only weakly reflects the ultrasound and has a low brightness. When such data is displayed in a typical three-dimensional representation, only the cardiac muscle portion having high brightness is displayed, and the inner cardiac cavity portion being hidden behind the cardiac muscle portion and not displayed. According to the present embodiment, in order to display the cardiac cavity portion, the brightness value is inverted, such that the cardiac muscle portion will have low brightness and the cardiac cavity portion will have high brightness, thereby making it possible to observe the cardiac cavity portion in a three-dimensional representation. An inverted image is created by processing the data stored in the three-dimensional data memory 20 by an inverted image forming section 22. The image processing performed by the inverted image forming section 22 will be described in detail below.

First, the brightness value of each voxel data in the three-dimensional data memory 20 is binarized in a binarization processing section 24. The threshold value used for binarization may be a predetermined fixed value or may be set by an operator in accordance with an ultrasonic image which is obtained. When the brightness data is based on 64 gray-scale levels, for each voxel, the brightness value is set to 0 when the brightness is lower than the threshold value, and the brightness value is set to 63 when the brightness value equals to or greater than the threshold value. Then, the brightness value is inverted in a brightness value inverting section 26. Because the brightness value has already been binarized, the brightness value is inverted from 0 to 63, or from 63 to 0 due to the inversion. Similar results can be obtained even when the order of performing the binarization and the inversion processing is reversed. When the inversion processing is performed prior to the binarization, in the case of 64 gray-scale levels, a processing is first performed in which the brightness is inverted from 0 to 63, from 1 to 62, from 2 to 61, . . . from 63 to 0. Subsequently, the inverted values are binarized using a predetermined threshold value.

Figure 3:
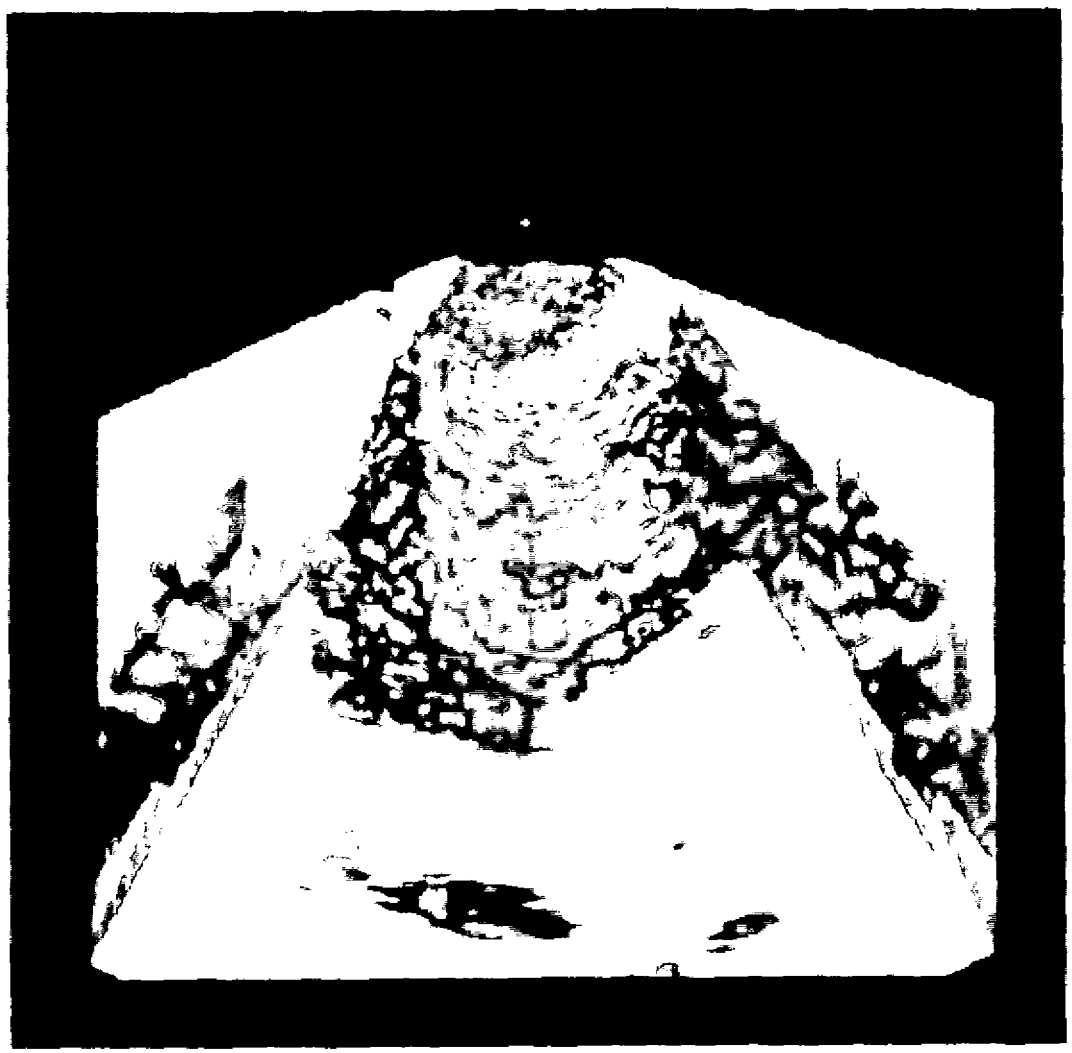
FIG. 3 is a view showing an example of an inverted and binarized ultrasonic image.

FIG. 3 shows an example image based on binarized and inverted data. In FIG. 3 is shown a state in which conversion from a polar coordinate system to a rectangular coordinate system has been performed. The surfaces which have an appearance similar to side surfaces of a quadrangular pyramid correspond to a portion where, perhaps due to the influence of a rib or the like, no reflection wave of ultrasound exists, and have appeared by inversion of the brightness values. The portion which seems to bulge in the middle of the drawing represents the cardiac cavity.

Although not shown in FIG. 3, when the binarized data is displayed without any processing, the display is inferior because the contrast is too high, and the noise is emphasized. It is therefore preferable to apply image processing such as the following to the binarized and inverted data so as to form and display a clear and useful image. First, noise removal is performed in a noise removing section 28. For example, on a θ-φ plane, with regard to eight voxels surrounding a certain target voxel, when at least five voxels have a brightness value of 63 (in the case of 64 gray-scale), the brightness value of the target voxel is set to 63. When four or less voxels have a brightness value of 63, the target voxel maintains its brightness value. Further, when at least five voxels surrounding the target voxel have a brightness value of 0, the brightness value of the target pixel is set to 0. When four or less voxels have a brightness value of 0, the target voxel maintains its brightness value. The noise removing processing which is performed on a θ-φ plane in the above description may also be performed on a θ-r plane or a φ-r plane. Further, the brightness value of a target voxel may be determined based on brightness values of 26 voxels three dimensionally surrounding the target voxel.

Subsequently, a smoothing processing is performed in a smoothing section 30. Because the binarized data is, as described above, not preferable, an image processing for obtaining a smooth display is performed. For example, smoothing can be achieved by determining the brightness value of a certain voxel to be an average of brightness values of the certain voxel and the surrounding voxels. In order to calculate the average value, 9 voxels within one plane or 27 voxels in a three-dimensional plane may be used. With such smoothing processing, voxels with a middle tone are generated, resulting in a smooth display. Further, in an interpolating section 32, interpolation between lines (in the θ direction) and between frames (in the φ direction) is performed.

Figure 4:
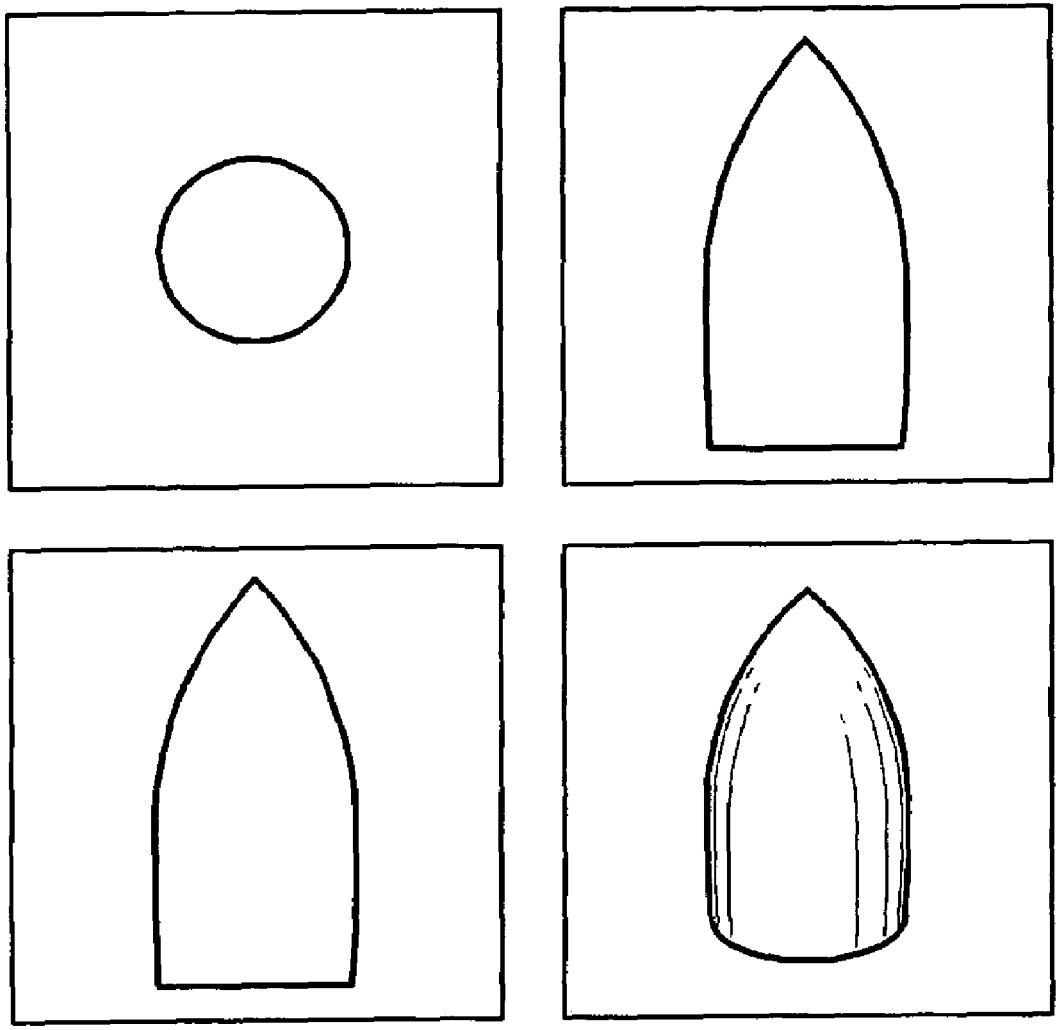
FIG. 4 is a view showing an example of region of interest for extracting the cardiac cavity portion.

Finally, extraction of a cardiac cavity portion is performed in a cardiac cavity portion extracting section 34. As also shown in FIG. 3, in an image which has been binarized and inverted, displayed images other than that of the cardiac cavity portion which is the object of observation obstruct observation of the cardiac cavity portion being observed. Therefore, the cardiac cavity portion is extracted using a general shape thereof. FIG. 4 shows an example of region of interest for extracting the cardiac cavity portion. Because the shape of the cardiac cavity portion can be outlined by a substantial ellipsoid, the region of interest is set to a substantial ellipsoid. In FIG. 4, the upper left view is a plan view of an ellipsoid, the lower left view is a front view thereof, the upper right view is a side view thereof, and the lower right view is a perspective view thereof. The shape (the length of a longer axis, the length of shorter axis, and so on) and the position of the ellipsoid is determined such that the cardiac cavity portion can be preferably extracted. Although the region of interest is preferably a substantial ellipsoid when a cardiac cavity portion is extracted, when other site is extracted, it is preferable that the region of interest having a shape in accordance with that target site is used for extraction.

A selector 36 selects either the original three-dimensional data or the extracted data of a cardiac cavity portion which has been binarized and inverted, according to an operator's instruction, and transmits the selected data to a converting section 38. The converting section 38 performs data conversion from a polar coordinate system to a rectangular coordinate system and also data conversion for two-dimensional display. When data stored in the three-dimensional data memory 20 is already converted to a rectangular coordinate system, only the data conversion for displaying three-dimensional data two-dimensionally is performed in the converting section 38. Then, a display is created on the monitor 17 using the converted data.

Further, a volume calculating section 40 calculates the volume of the cardiac cavity portion based on the data of the cardiac cavity portion extracted by the cardiac cavity portion extracting section 34. Because the extracted cardiac cavity portion is a solid model, the volume can be obtained with higher degree of accuracy than when the volume is assumed from the length of a part of the cardiac cavity portion or from a cross sectional area in one section of the cardiac cavity portion. In addition, information supporting a diagnosis, such as, for example, a change of the volume with time, the maxim and minimum values of the volume, and a stroke volume corresponding to the difference between the maxim and minimum volumes, are also calculated. All or some portion of the calculated data is displayed on the monitor 17.

Figure 5:
FIG. 5 is an example image of an extracted cardiac cavity portion which has been binarized and inverted.

FIG. 5 shows an example of an image of the extracted cardiac cavity portion. The viewing point can be changed by user operation of the operation panel 14, so that the rear side in the display of FIG. 5 can also be observed.

While in the foregoing embodiment, processing in which the brightness value is both inverted and binarized is performed, it is also possible to display data which has only been inverted, and has not been binarized.

As described above, a cavity portion of an organ, which normally has a low brightness, is made bright by inverting the brightness value of an obtained ultrasonic image, and three-dimensional display of the cavity portion is performed. As a result, the shape of the cavity portion can be easily understood and the accuracy of calculating the volume of the cavity portion can be increased.

While the preferred embodiment of the present invention has been described using specific terms, such description is for illustrative purposes only, and it is to be understood that changes and variations may be made without departing from the spirit or scope of the appended claims.

What is claimed is:

1. An ultrasonic diagnostic apparatus for transmitting and receiving an ultrasonic wave with regard to a living body and providing a three-dimensional image of an organ based on the received ultrasonic wave, comprising:
    a means for inverting a brightness value of each voxel regarding three-dimensional data obtained from received ultrasonic signal so as to display a cavity portion of the organ, and a three-dimensional image of the cavity portion of the organ is provided based on the inverted data;
    a means for binarizing the brightness value before or after inversion of the brightness value of each voxel,
    a means for setting a region of interest outside a target portion so as to surround the target, portion; and
    a means for three-dimensionally displaying inverted and binarized voxels present within the set region of interest.

2. An ultrasonic diagnostic apparatus according to claim 1, comprising:
    a means for calculating and providing a volume of the cavity portion of the organ based on the three-dimensional image of the cavity portion.

3. An ultrasonic diagnostic apparatus according to claim 2, comprising:
    a means for calculating and providing data for supporting diagnosis based on a result of the calculation of the volume of the cavity portion.

4. An ultrasonic diagnostic apparatus according to claim 1, wherein the organ to be observed is a heart.

5. An ultrasonic diagnostic apparatus according to claim 4, wherein
    the cavity portion to be observed is the left ventricle.

* * * * *